Figure 1:
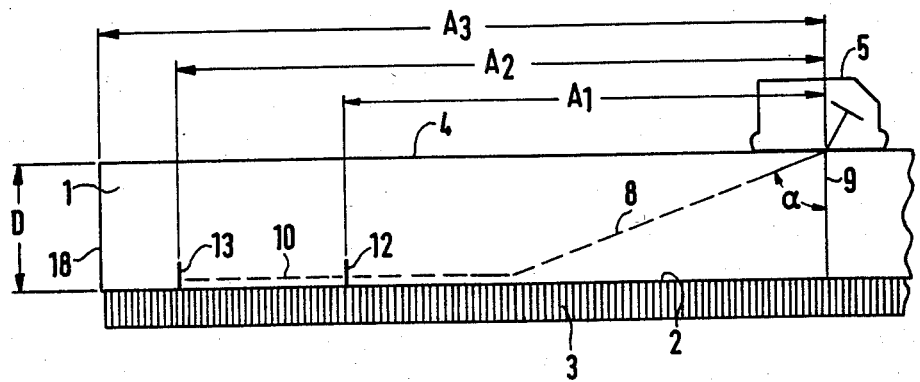

United States Patent [19]

Heumüller

[11] Patent Number: 4,603,583
[45] Date of Patent: Aug. 5, 1986

[54] METHOD FOR THE ULTRASONIC TESTING OF FERRITIC PARTS HAVING A CLADDING

[75] Inventor: Roland Heumüller, Erlangen, Fed. Rep. of Germany

[73] Assignee: Kraftwerk Union Aktiengesellschaft, Mülheim, Fed. Rep. of Germany

[21] Appl. No.: 718,062

[22] Filed: Apr. 1, 1985

[30] Foreign Application Priority Data

Apr. 6, 1984 [DE] Fed. Rep. of Germany ....... 3413097

[51] Int. Cl.⁴ .............................................. G01N 29/04
[52] U.S. Cl. .......................................... 73/596; 73/629
[58] Field of Search .................. 73/596, 629, 644, 588

[56] References Cited

U.S. PATENT DOCUMENTS 4,170,143 10/1979 Ries et al. ................................ 73/629
4,467,653 8/1984 Turbe .................................... 73/629

FOREIGN PATENT DOCUMENTS 0184507 10/1983 Japan ..................................... 73/629
780752 8/1957 United Kingdom .................. 73/629

*Primary Examiner*—Anthony V. Ciarlante
*Attorney, Agent, or Firm*—Herbert L. Lerner; Laurence A. Greenberg

[57] ABSTRACT

Method for the ultrasonic testing of ferritic bodies having a cladding surface, a surface opposite the cladding surface, a cladding disposed on the cladding surface, an ultrasound transmitter radiating from the surface opposite the cladding surface into the body at an angle relative to the cladding surface, and a receiver for receiving reflections emanating from a fault in the body, which includes radiating longitudinal waves from the transmitter into the body at an angle between 70° and 86° relative to the perpendicular.

4 Claims, 2 Drawing Figures

METHOD FOR THE ULTRASONIC TESTING OF FERRITIC PARTS HAVING A CLADDING

The invention relates to a method for the ultrasonic testing of ferritic components having a cladding, including an ultrasound transmitter which radiates into the part on the surface of the part facing away from the cladding and at an angle to the cladding surface, and a receiver for reflected sinals emanating from a fault.

With prior art methods, the sensitivity of the test and thereby, the probability of finding faults in a zone close to the cladding, is adversely affected by background noise which emanates from from the cladding. On the other hand, it is essential during production and in-service testing to measure accurately in the region close to the cladding, so that even small incipient cracks are reliably detected.

It is accordingly an object of the invention to provide a method for the ultrasonic testing of ferritic parts having a cladding which overcomes the hereinafore-mentioned disadvantages of the heretofore-known methods of this general type.

With the foregoing and other objects in view there is provided, in accordance with the invention, a method for the ultrasonic testing of ferritic bodies having a cladding surface, a surface opposite the cladding surface, a cladding disposed on the cladding surface, an ultrasound transmitter radiating from the surface opposite the cladding surface into the body at an angle relative to the cladding surface, and a receiver for receiving reflections emanating from a fault in the body, which includes radiating longitudinal waves from the transmitter into the body at an angle between 70° and 86° relative to the perpendicular.

It has amazingly been found that with the method according to the invention, accurate and heretofore unachieved measurements are possible, because the longitudinal wave releases a wave at the cladding plane traveling parallel to the interface. This wave, which heretofore obviously has never been detected, is only minimally sensitive to structure-related backscatter, so that a correspondingly large margin or ratio of signal to noise is obtained. In addition, this wave strikes cracks under the cladding lying in the cladding plane, so that such faults can be sensitively detected, even if they have small dimensions. The useful range of this wave is at least 400 mm, if the surface of the part or body provided for the cladding is straight. Freedom of the parts from faults can therefore be demonstrated with far fewer testing head movements than heretofore.

In accordance with another feature of the invention, there is provided adjusting the radiating angle from the transmitter for focusing the ultrasound beam on the cladding. In this way, the sensitivity can be further increased. Focusing can be accomplished by conventional means, and more specifically for a single-vibrator test head as well as for a transmitter/receiver test head.

In accordance with a concomitant feature of the invention, there is provided separating the receiver from the ultrasound transmitter up to a distance from the fault substantially equal to 0.7 times the thickness of the body. This is possible as long as the receiver is not identical with the transmitter. The minimum distance from the transmitter is given as the distance for the direct insonification of the fault, depending on the angle. The thickness of the part is understood in this context to mean the perpendicular distance between the cladding plane and the surface of the part opposite the cladding surface.

Other features which are considered as characteristic for the invention are set forth in the appended claims.

Although the invention is illustrated and described herein as embodied in method for the ultrasonic testing of ferritic parts having a cladding, it is nevertheless not intended to be limited to the details shown, since various modifications may be made therein without departing from the spirit of the invention and within the scope and range of equivalents of the claims.

Figure 2:
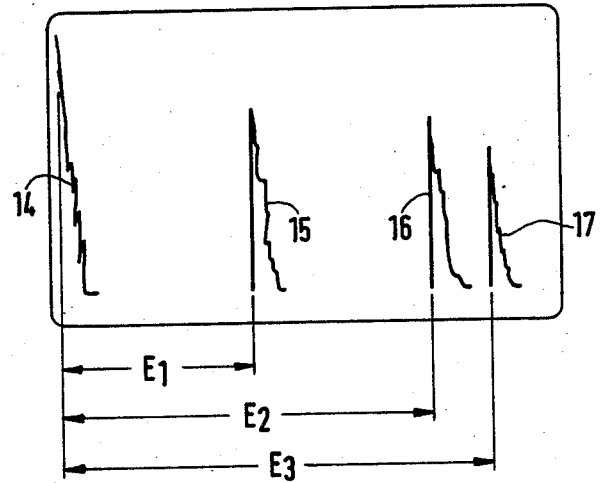

The invention, however, together with additional objects and advantages thereof will be best understood from the following description when read in connection with the accompanying drawing, in which:

FIG. 1 is a fragmentary, diagrammatic, cross-sectional view of a body to be tested with the method according to the invention; and FIG. 2 is a front elevational view of a picture screen showing echoes.

Referring now to the figures of the drawings in detail and first particularly to FIG. 1 thereof, there is seen a planar test body 1 formed of ferritic material which is provided with a cladding 3 on a lower surface or cladding plane 2 thereof. A test head 5 is placed on a surface 4 opposite the cladding 3. The test head 5 may be a single-vibrator test head or a transmitter and receiver test head which generates an ultrasonic beam in a conventional manner. The ultrasound or ultrasonic beam is indicated in FIG. 1 by a main beam 8 shown in broken lines, and is radiated on the cladding plane at an angle $\alpha$ relative to the perpendicular 9 on the cladding plane 2. The angle $\alpha$ is between 70° and 80°. In this region, the main beam 8 which is radiated-in as a longitudinal wave and is focused on the cladding 3, leads to a wave 10 which is parallel to the interface between the body 1 and the cladding 3. A high detection sensitivity for faults in the region near the cladding is obtained with this wave parallel to the interface. In the illustrated embodiment, such faults are indicated at reference numerals 12 and 13.

The above-mentioned faults 12, 13 lead to clearly distinguishable fault echoes on a picture screen shown in FIG. 2, which is associated with the receiver of the ultrasound system. The fault 12 which is disposed at a distance $A_1$ from the testing head 5, appears on the picture screen as an echo 15. A delay $E_1$ of the echo 15 from a time 14 signifying the entrance of the sound into the steel or ferritic material of the body 1 (zero position of the picture screen), is proportional to the fault distance $A_1$. The second fault 13 results in a reflection signal 16, having a delay $E_2$ relative to the sound entrance 14 which is again proportional to the fault distance $A_2$ between the fault 13 and the test head 5.

A further reflection signal 17 is indicated in FIG. 2. This signal comes from the rear side 18 of the test body. The delay $E_3$ of of the signal 17 is proportional to the distance $A_3$ between the rear wall 18 and the sound emission point of the transmitter 5.

In FIG. 1, the thickness D of the ferritic body 1 is assumed to be 30 mm. The thickness of the cladding is 5 mm, for instance. The special sensitivity obtained with the method according to the invention, can be expected up to a distance between test head 5 and the fault which is 0.7 times the thickness of the body 1. In the illustrated embodiment, this means that a receiver test head which may be separated from the transmitter, can be moved so that the point of its sound emission is 21 mm from the faults 12, 13.

The foregoing is a description corresponding, in substance, to German application P 34 13 097.7, dated Apr. 6, 1984, International priority of which is claimed for the instant application, and which is hereby made part of this application. Any material discrepancies between the foregoing specification and the specification of the aforementioned corresponding German application are to be resolved in favor of the latter.

There are claimed:

1. Method for the ultrasonic testing of ferritic bodies having a cladding surface for faults in the cladding surface, a surface opposite the cladding surface, a cladding disposed on the cladding surface, an ultrasound transmitter radiating from the surface opposite the cladding surface into the body at an angle relative to the cladding surface, and a receiver disposed on the surface opposite the cladding surface, for receiving reflections emanating from a fault in the body, which comprises radiating longitudinal waves from the transmitter into the body at an angle between 70° and 86° relative to the perpendicular to the cladding surface causing the waves to travel in a direction substantially parallel to the cladding surface in the body.

2. Method according to claim 1, which comprises adjusting the radiating angle from the transmitter for focusing the ultrasound beam on the cladding.

3. Method according to claim 1, which comprises separating the receiver from the ultrasound transmitter up to a distance from the fault substantially equal to 0.7 times the thickness of the body.

4. Method according to claim 2, which comprises separating the receiver from the ultrasound transmitter up to a distance from the fault substantially equal to 0.7 times the thickness of the body.

* * * * *